United States Patent [19]
O'Connor

[11] Patent Number: 5,603,724
[45] Date of Patent: Feb. 18, 1997

[54] SUCTION PUNCH

[75] Inventor: Paul D. O'Connor, East Bridgewater, Mass.

[73] Assignee: TNCO, Inc., Whitman, Mass.

[21] Appl. No.: 387,312

[22] Filed: Feb. 13, 1995

[51] Int. Cl.$^6$ ........................................... A61B 17/00
[52] U.S. Cl. ......................... 606/207; 604/22; 128/751; 606/174; 606/184
[58] Field of Search ............................ 606/51, 52, 174, 606/205–211, 184; 128/750–755; 604/22

[56] References Cited

U.S. PATENT DOCUMENTS

| | | |
|---|---|---|
| 3,980,086 | 9/1976 | Kletschka et al. . |
| 4,522,206 | 6/1985 | Whipple et al. . |
| 5,217,460 | 6/1993 | Knoepfler .................................. 606/52 |
| 5,417,709 | 5/1995 | Slater ....................................... 606/207 |

*Primary Examiner*—Michael Powell Buiz
*Assistant Examiner*—William Lewis
*Attorney, Agent, or Firm*—Stephen Y. Chow; Jerry Cohen; Edwin H. Paul

[57] ABSTRACT

A cutting-suctioning tool for micro-surgery including closing jaws, that in closed position, provide a suctioning/fluid channel axially through the jaws for removal of tissue and fluids.

14 Claims, 7 Drawing Sheets

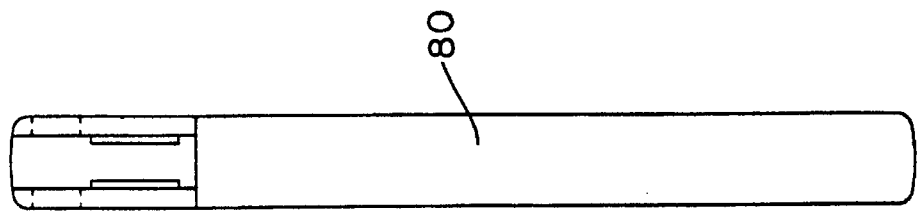
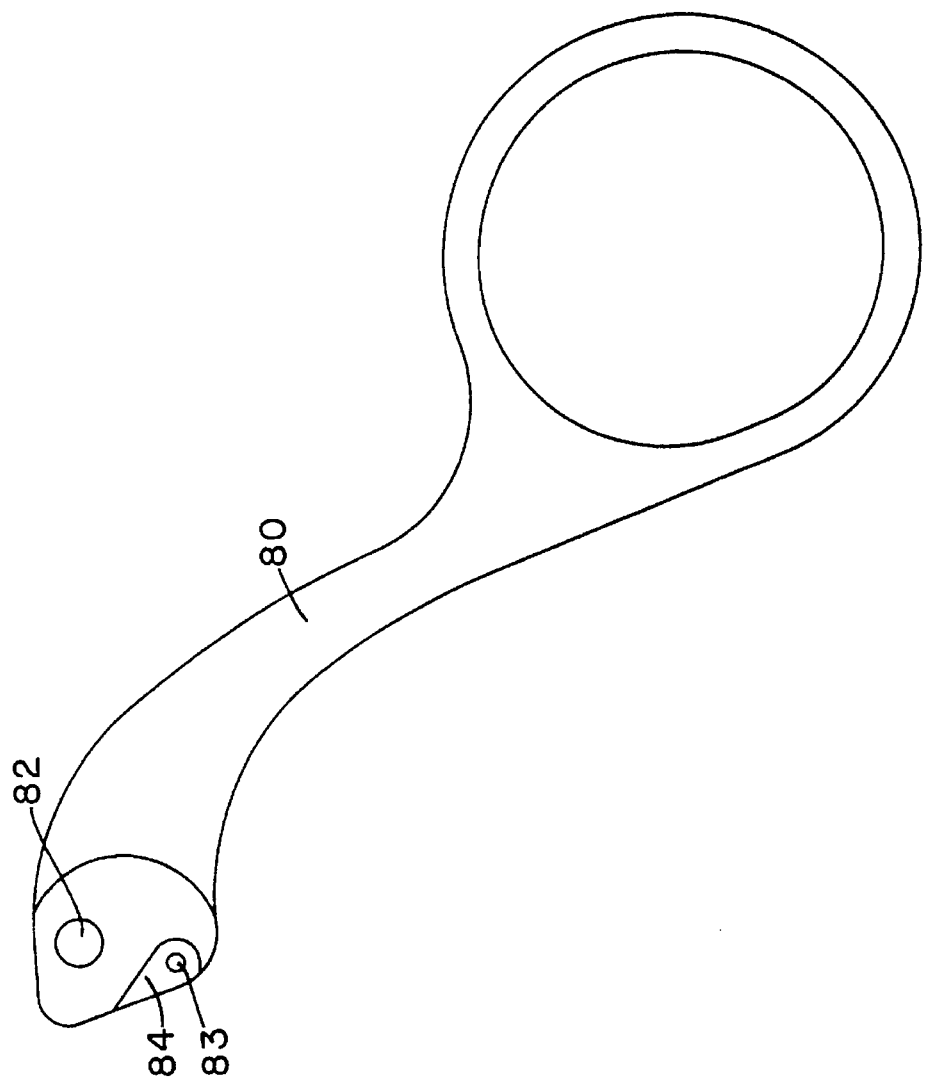

SUCTION PUNCH

BACKGROUND OF THE INVENTION

The field of the invention is that of micro-instrumentation, that is, articulating, hand-held, instruments used in micro-surgery and like applications, for cutting or punching out tissue. The invention is particularly advantageous for endoscopic, or minimally invasive, surgery, where removal of cut or punched out tissue or fluids by vacuum evacuation is useful, such as in cutting sinus tissue.

The state of the prior art includes U.S. Pat. No. 4,522,206, to Whipple, et al. There, a cutting-suctioning instrument is disclosed in which "a surgical instrument is specifically constructed to have an open throat between proximal portions of distal jaws constructed and arranged, when open, to provide a distally-directed, end aperture through which tissue can enter." (Col. 1, lines 39–43.) The disclosed instrument does not allow suctioning when the jaws are closed. Moreover, when the jaws are open, the suctioning is provided between the proximal ends of the jaws, not the distal end of the instrument. The Whipple device thus has the disadvantage of not providing, or providing only disappated suction at the very distal end of the instrument where cut tissue or fluids may be pooled.

SUMMARY OF THE INVENTION

Objectives of the present invention include the provision of an endoscopic instrument that is capable of transmitting maximum force to its jaws to cut through tough tissue and to perform suctioning at the distal tip of the instrument when the jaws are closed. This is accomplished in part by providing a fluid or vacuum channel through the jaws of the instrument in their closed position.

The present invention comprises a hollow tubular drive member with an end bearing which engages a movable punch jaw to push it around a pivot to close the jaw in engagement with an opposing jaw and thereby cut tissue between the jaws. In its closed position, a suctioning path is provided through both jaws to the distal tip of the instrument, said path connected in a sealed path to the hollow of the drive member, which provides the suctioning force to draw fluid and tissue from the distal end of the instrument to the proximal (external) end. In the open position of the jaws, the suction path is broken.

DESCRIPTION OF THE DRAWINGS

FIG. 9A is a side view of the moving loop handle of the micro-instrument.

FIG. 9B is a distal view of the moving loop handle of the micro-instrument.

FIG. 10 is a side view of the instrument.

DETAILED DESCRIPTION

Figure 1:
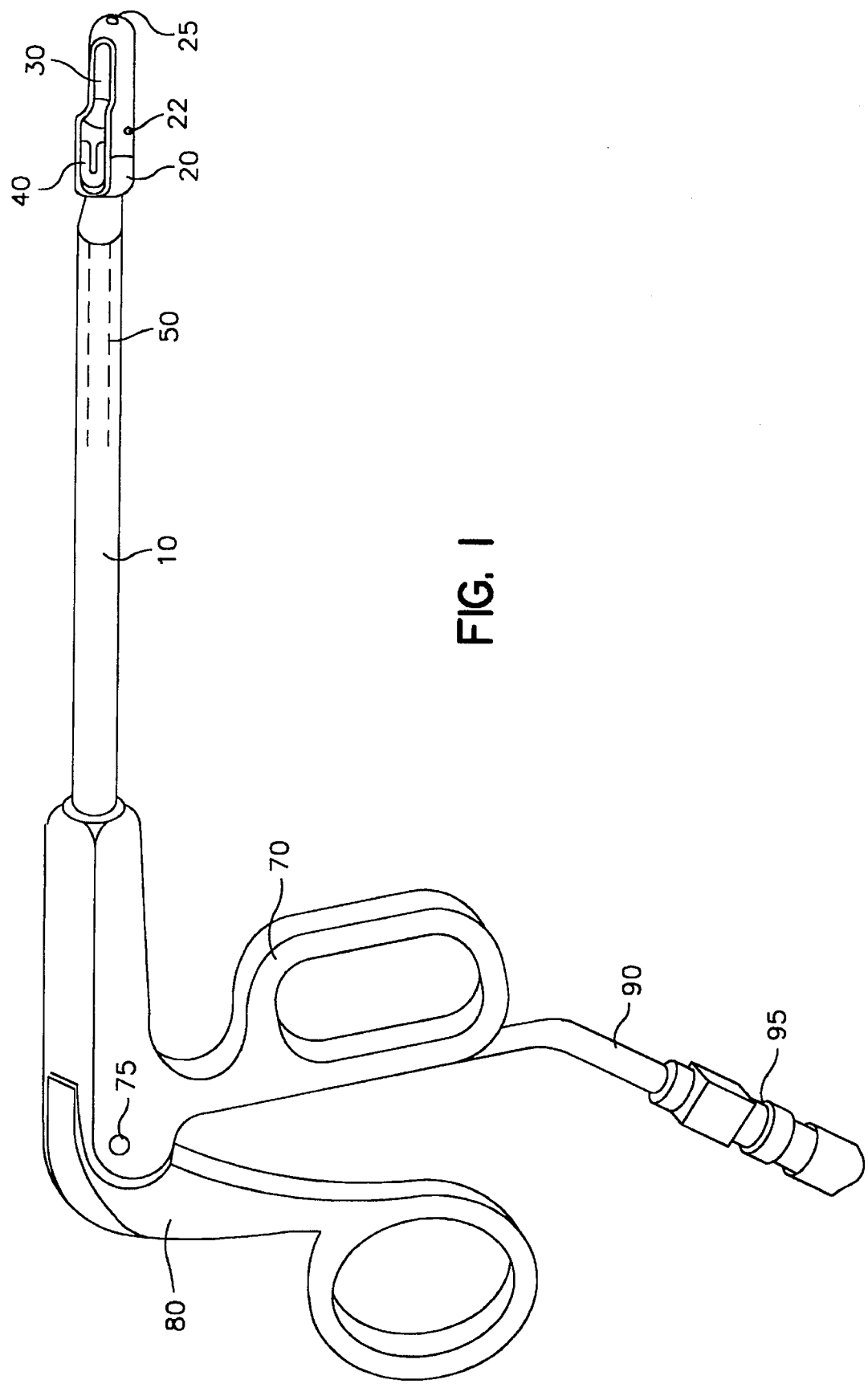
FIG. 1 is a perspective view of a micro-instrument including the invention with the jaws in closed position.
Figure 2:
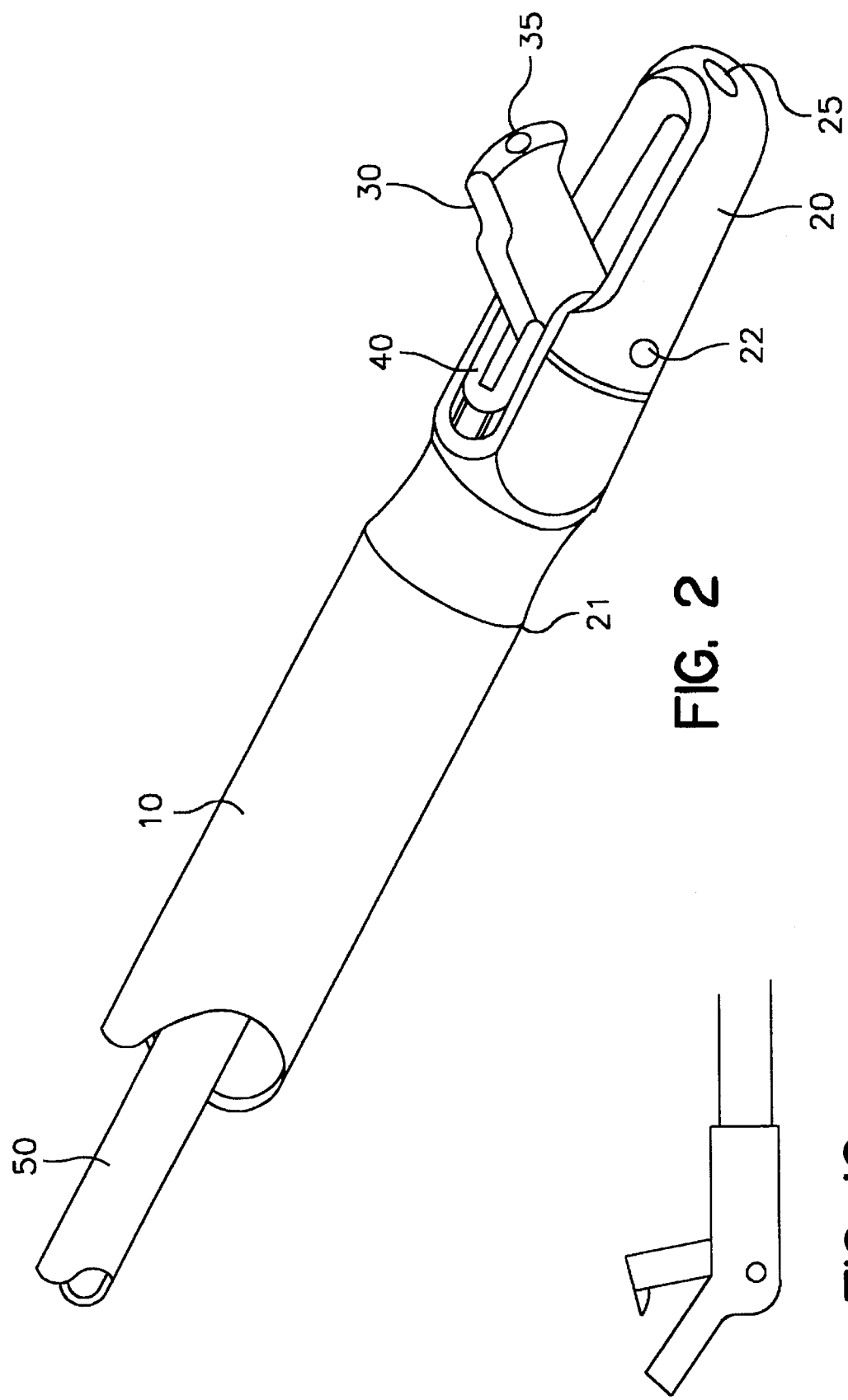
FIG. 2 is a perspective view of the micro-instrument in its front section with the jaws in open position.

FIG. 1 shows a perspective view of a micro-instrument embodying the invention with the cutting jaws in closed position. Tubular extension 10 of 4–10 inches long and 3–5 mm in diameter connects the cutting tip assembly 20, 30 and 40 with the supporting stationary loop handle 70 and the actuating loop handle 80. Actuation force transmitted is transmitted by internal drive tube 50 which comprises a fluid or vacuum channel connecting distal port 25 and the handle suction tube 90 with suction connection 95. As the actuating loop handle 80 is rotated on pivot 75 away from stationary loop handle 70, the drive tube 50 is drawn proximally to rotate, by means of linkage 40 the distal portion of inner tip or jaw 30 on pivot 22 away from the distal portion outer tip or jaw 20 to its open position shown in FIG. 2, which also shows the welding 21 and the distal port 35 of inner tip or jaw 30 which lines up and communicates fluid or suction with distal port 25 of outer tip or jaw 20.

Figure 3:
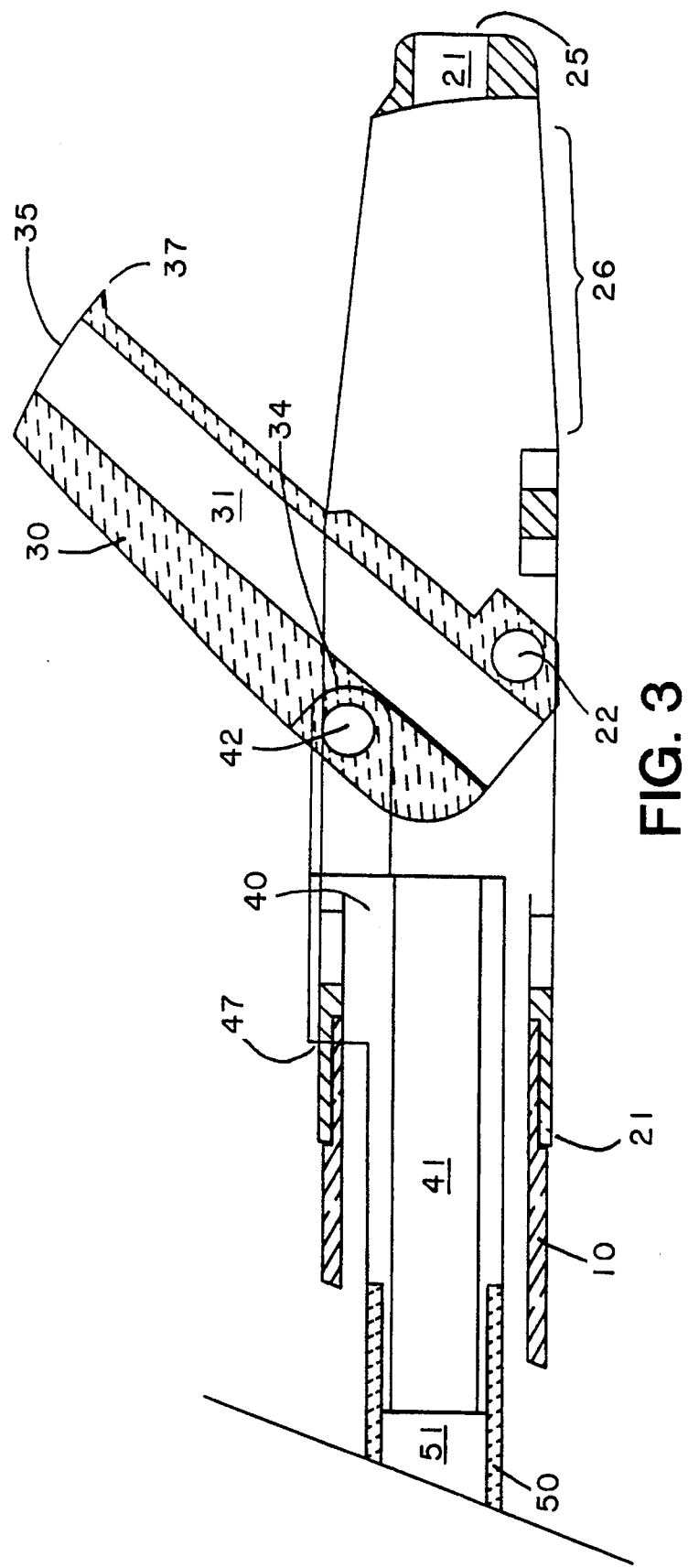
FIG. 3 is a cross-sectional view of the tip section of the micro-instrument.
Figure 5A:
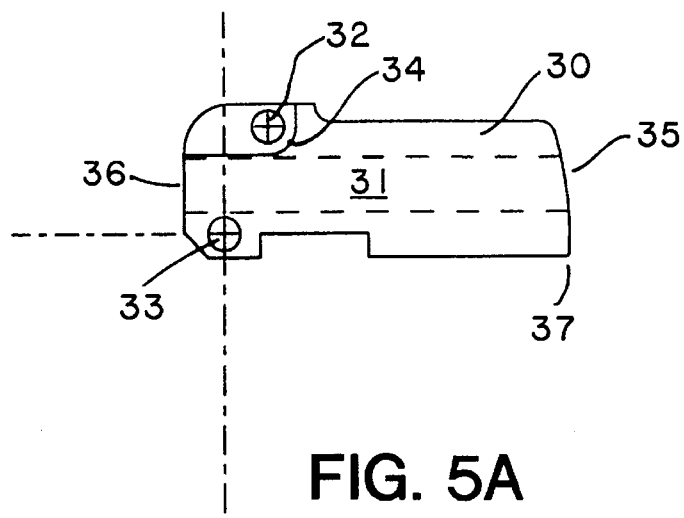
FIG. 5A is a side view of the inner tip of the micro-instrument.
Figure 5B:
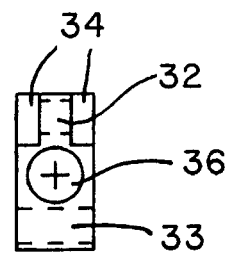
FIG. 5B is a proximal axial view of the inner tip of the micro-instrument.
Figure 6A:
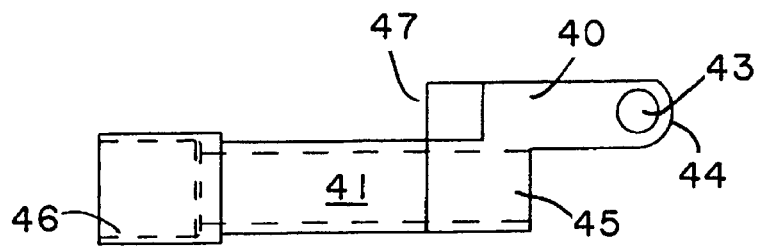
FIG. 6A is a side view of the actuator link of the micro-instrument.
Figure 6B:
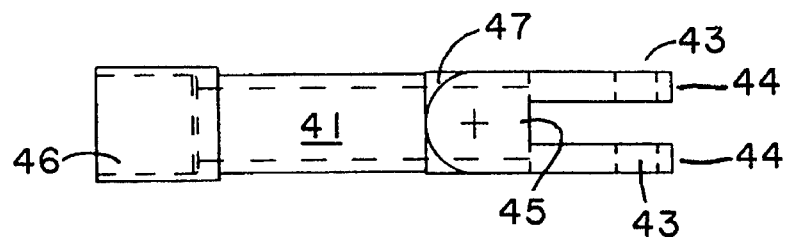
FIG. 6B is a top view of the actuator link of the micro-instrument.

FIG. 3 shows a cross-section of the assembled tip in open position with actuator link 40 positioned at the distal portion of drive tube 50 and engaging inner tip or jaw 30 at pin 42 and bearing surface 34. Inner tip or jaw 30 in turn pivots on pivot 22, which may be a hollow pin. Bearing surface 34 is shown in greater detail in FIGS. 5A and 5B respectively showing a side and a proximal end view of inner tip 30. Pin 42 shown in FIG. 3 fits through aperture 32 in inner tip 30 shown in FIGS. 5A and 5B and through apertures 43 in actuator link 50 shown in FIGS. 6A and 6B to transmit proximally directed pulling force to open the jaws and to share with bearing surfaces 44 (FIGS. 6A and 6B) and 34 (FIGS. 3, 4A and 4B) to transmit distally directed pushing force to close the jaws. The later force-distributing mechanism makes the instrument particularly effective in its cutting action.

Figure 7A:
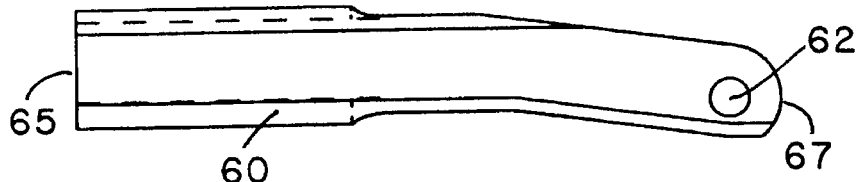
FIG. 7A is a side view of the proximal suction sleeve of the micro-instrument.
Figure 7B:
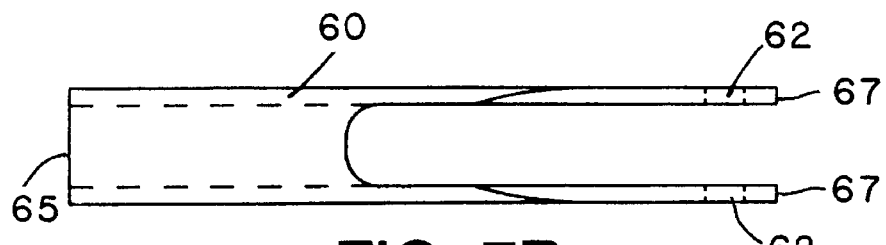
FIG. 7B is a top view of the proximal suction sleeve of the micro-instrument.
Figure 7C:
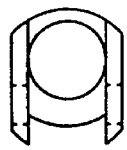
FIG. 7C is a proximal axial view of the proximal suction sleeve of the micro-instrument.

As the actuating tube 50 and actuating link 40 is pushed distally, and the inner tip 30 is rotated into closed position, port 45 of actuator link 40 (FIGS. 6A and 6B) is brought into sealed communication with rear port 36 of inner tip 30 (FIGS. 5A and 5B) and distal port 35 of inner tip 30 is brought into sealed communication with channel 21 and port 25 of outer tip 20, thus providing communication from channel 51 of actuating tube 50 through channel 31 of inner tip 30 through channel 21 of outer tip 20 to the distal port 25 of the micro-instrument. Thus a vacuum/fluid path is provided from the distal end of the instrument through the actuating tube 50 to the proximal handle suction tube 90 (FIG. 1) by way of proximal suction sleeve 60 (FIGS. 7A, 7B, and 7C) welded at port 65 to the proximal end of the actuating tube 50.

Figure 4A:
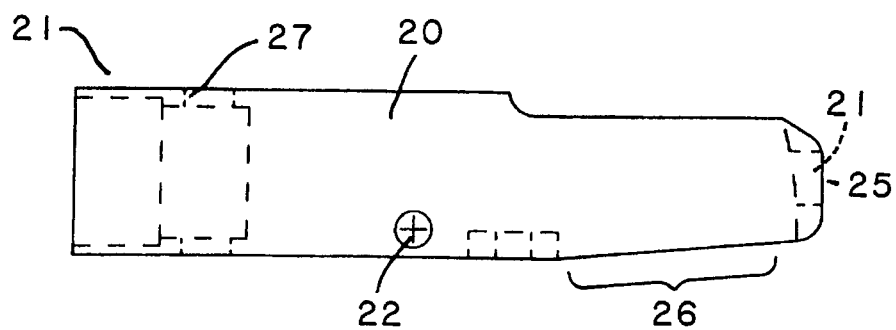
FIG. 4A is a side view of the outer tip of the micro-instrument.
Figure 4B:
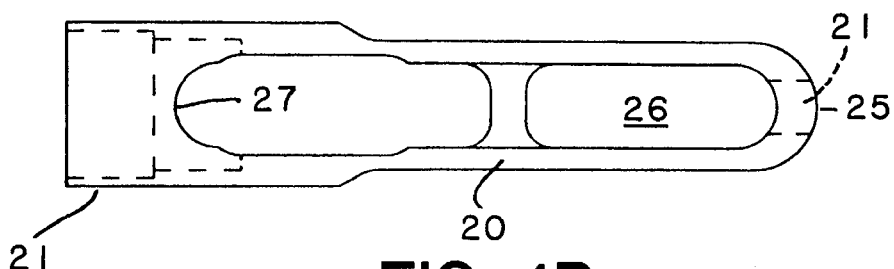
FIG. 4B is a top view of the outer tip of the micro-instrument.

As the inner tip 30 closes within outer tip 20, material is cut or punched by the sharp edge 37 (FIGS. 3, 5A and 5B) through aperture 26 in the outer tip 20 (FIGS. 4A and 4B). Buttress surface 27 in outer tip 20 (FIGS. 4A and 4B) provide a limit to the proximal movement of actuator link 40 by engaging stop surface 47 (FIGS. 6A and 6B) and thus limiting the opening of tip or jaw 30 (for example, a 7 mm opening between the distal ends of tips 20 and 30).

Figure 8C:
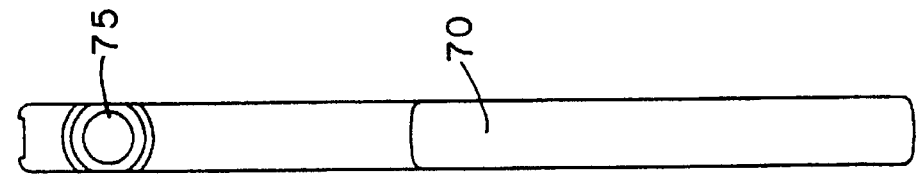
FIG. 8C is a distal view of the stationary loop handle of the micro-instrument.
Figure 8B:
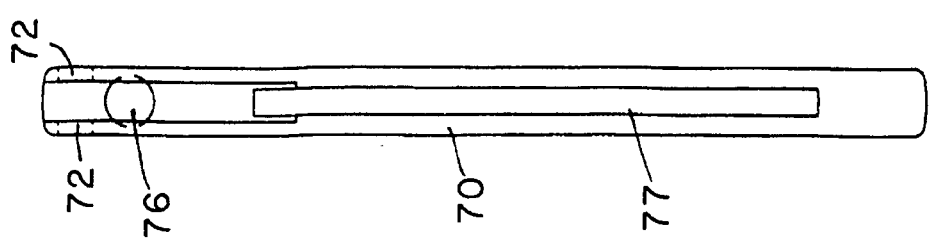
FIG. 8B is a proximal view of the stationary loop handle of the micro-instrument.
Figure 8A:
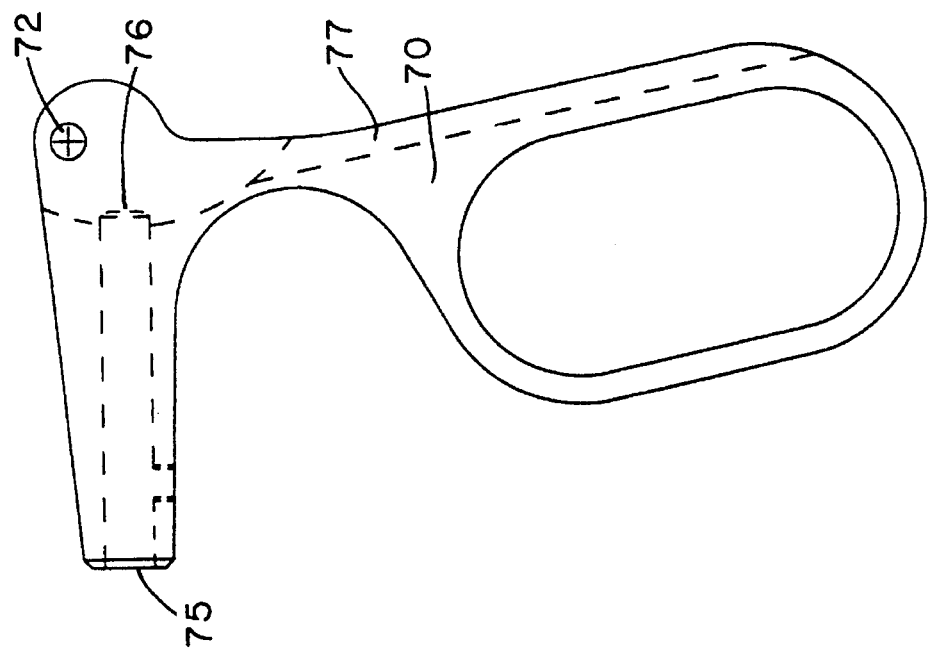
FIG. 8A is a side view of the stationary loop handle of the micro-instrument.

FIGS. 8A, 8B, and 8C show, respectively, side, rear and front views of the stationary loop handle 70. Extension tube 20 (FIG. 1) is attached to port 75, and actuating tube 50, terminating proximally with proximal vacuum sleeve 60 (FIGS. 7A, 7B and 7C) extends proximally beyond port 76. A channel 77 is provided for handle suction tube 90 (FIG. 1). FIGS. 9A and 9B show, respectively, side and front views of the moving loop handle 80, which pivots on pivot 75 (FIG. 1) inserted through apertures 72 on stationary loop handle 70 (FIGS. 8A and 8B) and aperture 82 on moving loop handle 80. Proximal vacuum sleeve 60 is attached to moving loop handle 80 using a pin or pivot inserted through aperture 83 in moving loop handle 80 (FIG. 9A) and apertures 62 on proximal vacuum sleeve 60, thus providing linkage for reciprocal motion of the actuating tube 50 to be transmitted to inner tip 30. Bearing surface 84 in moving loop handle 80 (FIG. 9A) distributes pushing force on bearing surfaces 67 of the proximal vacuum sleeve 60 (FIGS. 7A and 7B) for more effective cutting.

In alternative embodiments, different pivoting schemes may be employed, including integral pivots instead of pins. Also, the cutting tip may be bent for access to different body cavities, such as shown in FIG. 10.

What is claimed is:

1. A miniature articulated tip tool assembly comprising:
   (a) an elongated housing defining a channel therein and having at a distal end thereof a pivotal mounting for at least one jaw member;
   (b) an elongated drive member positioned within said channel terminating substantially at its distal end with at least one linking means;
   (c) a first jaw member (i) mounted for rotation on said pivotal mounting; (ii) engaging said drive member linking means for rotating said jaw member reciprocally towards or away from a second jaw member; and (iii) provided with a fluid channel axially therethrough;
   (d) said second jaw member (i) attached to said elongated housing; and (ii) provided with a fluid channel axially therethrough;
   such that when said first jaw member is rotated toward said second jaw member into axial alignment with said second jaw member, each of said fluid channels are axially aligned and a sealed path is provided through the fluid channels of said jaw members to the distal tip of said tool assembly.

2. The apparatus of claim 1 wherein the drive member linking means includes a distal end surface that engages a bearing surface on said first jaw to transmit distally-directed pushing force.

3. The miniature articulated tip tool assembly of claim 1 in which said first and second jaw members are shaped to engage in said axially aligned position to provide a cutting action in the process of rotating to said axially aligned position.

4. The miniature articulated tip tool assembly of claim 1 wherein said drive member is provided with a fluid channel axially therethrough which forms part of the sealed path when said first jaw is rotated towards said second jaw into axial alignment with said second jaw.

5. A miniature articulated tip tool assembly comprising:
   (a) an elongated housing defining a channel therein and having at a distal end thereof a pivotal mounting for at least one jaw member;
   (b) an elongated drive member positioned within said channel terminating substantially at its distal end with at least one linking means;
   (c) a first jaw member (i) mounted for rotation on said pivotal mounting; (ii) engaging said drive member linking means for rotating said jaw member reciprocally towards or away from a second jaw member; (iii) engaging said second jaw member when rotated towards said second jaw member along a sharp edge provided on said first jaw member; and (iv) provided with a fluid channel axially therethrough;
   (d) said second jaw member (i) attached to said elongated housing; and (ii) provided with a fluid channel axially therethrough;
   such that when said first jaw member is rotated towards said second jaw member into axial alignment with said second jaw member, a cutting action is provided at said sharp edge provided on said first jaw member and a sealed path is provided through the fluid channels of said jaw members to the distal tip of said tool assembly.

6. The miniature articulated tool assembly of claim 5 in which said first jaw is rotated towards said second jaw by a pushing action of said drive member engaging said first jaw at its distal end.

7. The miniature articulated tool assembly of claim 5 wherein said second jaw forms a loop attached at its ends to said elongated member and said first jaw fits in close engagement within said loop when said first jaw is rotated towards said second jaw into axial alignment with said second jaw.

8. The miniature articulated tool assembly of claim 7 in which said first jaw is rotated towards said second jaw by a pushing action of said drive member engaging said first jaw at its distal end.

9. The miniature articulated tool assembly of claim 7 wherein said loop is "U"-shaped.

10. The miniature articulated tool assembly of claim 9 in which said first jaw is rotated towards said second jaw by a pushing action of said drive member engaging said first jaw at its distal end.

11. The miniature articulated tip tool assembly of claim 5 wherein said drive member is provided with a fluid channel axially therethrough which forms part of the sealed path when said first jaw is rotated towards said second jaw into axial alignment with said second jaw.

12. The miniature articulated tool assembly of claim 11 in which said first jaw is rotated towards said second jaw by a pushing action of said drive member engaging said first jaw at its distal end.

13. The miniature articulated tool assembly of claim 12 wherein said second jaw forms a loop attached at its ends to said elongated member and said first jaw fits in close engagement within said loop when said first jaw is rotated towards said second jaw into axial alignment with said second jaw.

14. The miniature articulated tool assembly of claim 13 wherein said loop is "U"-shaped.

* * * * *